United States Patent
Yamamoto et al.

(10) Patent No.: US 11,046,772 B2
(45) Date of Patent: Jun. 29, 2021

(54) PROCESS OF PRODUCTION WITH CONTROLLED COPPER IONS

(71) Applicant: Chugai Seiyaku Kabushiki Kaisha, Tokyo (JP)

(72) Inventors: Seiko Yamamoto, Tochigi (JP); Hiroyuki Doi, Tokyo (JP); Isamu Terashima, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/561,154

(22) PCT Filed: Mar. 25, 2016

(86) PCT No.: PCT/JP2016/059634
§ 371 (c)(1),
(2) Date: Sep. 25, 2017

(87) PCT Pub. No.: WO2016/153041
PCT Pub. Date: Sep. 29, 2016

(65) Prior Publication Data
US 2018/0051090 A1 Feb. 22, 2018

(30) Foreign Application Priority Data
Mar. 26, 2015 (JP) .............................. JP2015-063662

(51) Int. Cl.
*C07K 16/28* (2006.01)
*A61K 38/00* (2006.01)
*C12N 5/00* (2006.01)
*C12N 5/071* (2010.01)
*C12P 21/00* (2006.01)

(52) U.S. Cl.
CPC .......... *C07K 16/2866* (2013.01); *A61K 38/00* (2013.01); *C12N 5/0018* (2013.01); *C12N 5/0682* (2013.01); *C12P 21/00* (2013.01); *C07K 2317/14* (2013.01); *C07K 2317/24* (2013.01); *C12N 2500/20* (2013.01); *C12N 2500/80* (2013.01); *C12N 2510/02* (2013.01)

(58) Field of Classification Search
CPC .... C12N 5/00; C12N 5/16; A61K 8/00; C12P 21/00
See application file for complete search history.

(56) References Cited

U.S. PATENT DOCUMENTS

| | | | |
|---|---|---|---|
| 2008/0124761 A1* | 5/2008 | Goto ..................... | C12N 5/0037 435/69.1 |
| 2010/0247523 A1 | 9/2010 | Kano et al. | |
| 2011/0117087 A1* | 5/2011 | Franze ................ | C07K 16/2866 424/133.1 |
| 2014/0206845 A1* | 7/2014 | Kameoka ............. | A61K 47/183 530/387.1 |

FOREIGN PATENT DOCUMENTS

| | | |
|---|---|---|
| JP | 2003334068 A | 11/2003 |
| JP | 3822137 B2 * | 9/2006 |
| JP | 2013533748 A | 8/2013 |
| JP | 2014113161 A | 6/2014 |
| WO | WO-2005090405 A1 | 9/2005 |
| WO | WO-2008109410 A1 | 9/2008 |
| WO | WO-2008131374 A1 | 10/2008 |
| WO | WO-2012006591 A1 | 1/2012 |
| WO | WO-2012006594 A1 | 1/2012 |
| WO | WO-2014145091 A1 | 9/2014 |
| WO | WO-20141459091 A1 | 9/2014 |
| WO | WO-2015024977 A1 | 2/2015 |
| WO | WO-2015143512 A2 | 10/2015 |

OTHER PUBLICATIONS https://chem.nlm.nih.gov/chemidplus/rn/375823-41-9, ChemIDplus, Tocilizumab RN 375823-41-9 (Year: 2020).*
Chaderjian et al., "Effect of Copper Sulfate on Performance of a Serum-Free CHO Cell Culture Process and the Level of Free Thiol in the Recombinant Antibody Expressed", Biotechnol Prog Mar.-Apr. 2005; 21(2):550-3 (Year: 2005).*
Babcock, J., et al., "Enhancing Performance in Cell Culture," Genetic Engineering & Biotechnology News 27(20), 4 pages (2014).
Media Formulation Products, Jul. 24, 2013, https://web.archive.org/web/20171110070027/http://www.sigmaaldrich.com:80/life-science/cell-culture/serum-free-media/media-formulation.html.
Invitation to Respond to Written Opinion in Singaporean Patent Application No. 11201707873T, dated Aug. 20, 2018.
Kaschak, T., et al., "Characterization of the basic charge variants of a human IgG1," mAbs 3(6):577-583 (2011).
Harris, R. J., "Processing of C-terminal lysine and arginine residues of proteins isolated from mammalian cell culture," Journal of Chromatography A 705:129-134 (1995).
Tsubaki, M., et al., "C-terminal modification of monoclonal antibody drugs: Amidated species as a general product-related substance," International Journal of Biological Macromolecules 52:139-147 (2013).
International Search Report for International Application No. PCT/JP2016/059634 dated Jun. 28, 2016, 2 pages.
Extended European Search Report dated Aug. 9, 2018, in European Application No. 16768944.7.
Gilbert, A., et al., "Identifying and eliminating cell culture process variability," Pharm Bioprocess., 2(6):519-534 (2014).

* cited by examiner

*Primary Examiner* — Ruth A Davis
(74) *Attorney, Agent, or Firm* — Nixon & Vanderhye P.C.

(57) ABSTRACT

The present invention provides a method of cell culture comprising adding a cell-containing seed medium to an initial medium and starting to culture the cell in the initial medium, wherein the initial medium has an organism-derived culture medium additive added thereto and the amount of the C-terminal amidated species in the produced protein is controlled by the copper content of the initial medium at the start of cell culture.

8 Claims, 2 Drawing Sheets

PROCESS OF PRODUCTION WITH CONTROLLED COPPER IONS

CROSS-REFERENCE TO RELATED APPLICATIONS

This application is a U.S. National Phase of PCT Application No. PCT/JP2016/059634, filed Mar. 25, 2016, which claims the benefit of Japanese Patent Application No. 2015-063662, filed Mar. 26, 2015, each of which is incorporated herein by reference.

TECHNICAL FIELD

The present invention relates to use of organism-derived culture medium additives in the manufacture of antibody drugs, and relates to a method of stabilizing the quality of antibody drugs by making use of the information about the copper content of the additives.

BACKGROUND ART

In culturing an animal cell in order to obtain a native protein that the animal cell produces or in culturing an animal cell transfected with a gene coding for a desired protein in order to obtain the desired protein or the like, not only basal nutrients such as salts, sugars, amino acids and vitamins but also organism-derived culture medium additives are usually added to the medium of use for the specific purpose of proliferating the animal cell, whereby a marked drop in the rate of cell survival in the early stage of culture is sufficiently prevented to maintain the number of viable cells in the culture broth and enable their prolonged culture. Further, from the viewpoint of manufacturing cost, the throughput of protein production is preferably as high as possible and, to this end, fed-batch culture is sometimes performed.

Meanwhile, speaking of the proteins such as antibody drugs that are produced by genetic recombination, they should theoretically have the amino acid sequences predicted from the genetic sequences but they may actually include various inhomogeneous components. This is due to either known or new in vivo (post-transcriptional (translational)) modifications or physicochemical (non-enzymatic) reactions (Harris R J., J Chromatogr A. 1995:705:129-134). Variations in the progress of these reactions will naturally lead to variations in the contents of inhomogeneous components in proteins. The variations in the inhomogeneous components in the proteins produced as active pharmaceutical ingredients are preferably as small as possible.

Among the inhomogeneous components contained in antibody drugs, molecular species amidated at the heavy chains' C-terminals are known (Tsubaki M et al., Int J Biol Macromol. 2013 January; 52:139-47; WO2005/090405). Although no reaction mechanism has been unraveled for the amidation of antibody drugs at C-terminals, it is known that the copper content in a medium used to produce an antibody drug by culturing animal cells is positively correlated with the amount of the C-terminal amidated species in the produced antibody drug (Kaschak T. et al., mAbs, 3:6, 577-583, 2011).

However, it has been entirely unknown that when an organism-derived culture medium additive is added to a culture medium and an antibody is produced by culture, the production of the additive involves so great a difference in copper content between lots that the content of the by-product C-terminal amidated species in the produced antibody varies on account of this lot-to-lot difference.

PRIOR ART LITERATURE

Patent Literature

Patent Document 1: WO2005/090405, titled "Subtypes of humanized antibody against interleukin-6 receptor"

Non-Patent Literature

Non-Patent Document 1: Harris R J. "Processing of C-terminal lysine and arginine residues of proteins isolated from mammalian cell culture" J Chromatogr A. 1995; 705:129-134

Non-Patent Document 2: Tsubaki M, Terashima I, Kamata K, Koga A "C-terminal modification of monoclonal antibody drugs: amidated species as a general product-related substance" Int J Biol Macromol. 2013 January; 52:139-47

Non-Patent Document 3: Kaschak T. et al. "Characterization of the basic charge variants of a human IgG1: effect of copper concentration in cell culture media" mAbs, 3:6, 577-583, 2011

SUMMARY OF INVENTION

Technical Problem

The present inventors first identified the problem that the production of organism-derived culture medium additives involves differences between lots that are extremely difficult to control to lie within limited ranges and which consequently cause variations in the quantity of the C-terminal amidated species in the antibodies produced by using such additives. Since antibody drugs desirably have the smallest possible variations in their inhomogeneity, the present inventors made intensive studies on a method to control the variations in the amount of the C-terminal amidated species in antibody production.

An object, therefore, of the present invention is to provide a means to control the amount of the C-terminal amidated species in the produced protein by culturing animal cells in a medium to which an organism-derived culture medium additive has been added.

Solution to Problem

As a result of the intensive studies made to solve the aforementioned problem, the present inventors developed a novel method of cell culture characterized in that individual production lots of an organism-derived culture medium additive are measured for their copper content and the lot selected by the measured copper content as an indicator is appropriately added to the culture medium, and have achieved the present invention.

The present invention is summarized below.

(1) A method of cell culture comprising adding a cell-containing seed medium to an initial medium and starting to culture the cell in the initial medium, wherein the initial medium has an organism-derived culture medium additive added thereto and the copper content of the initial medium at the start of cell culture is no more than 0.02 ppm.

(2) The method according to (1), wherein the copper content of the initial medium at the start of cell culture is no more than 0.015 ppm.

(3) The method according to (1) or (2), wherein an organism-derived culture medium additive with a copper content of no more than 1 ppm has been added to the initial medium.
(4) The method according to (3), wherein an organism-derived culture medium additive with a copper content of no more than 1 ppm has been added to the seed medium which is to be added to the initial medium.
(5) The method according to any one of (1) to (4), wherein the method of culture is batch culture, fed-batch culture, continuous culture, batch culture, or semi-batch culture.
(6) The method according to any one of (1) to (4), wherein the method of culture is fed-batch culture.
(7) The method according to (6), wherein an organism-derived culture medium additive with a copper content of no more than 3 ppm has been added to a fed-batch medium which is to be added to the initial medium.
(8) The method according to (6) or (7), wherein the copper ions derived from the fed-batch medium are present at no more than 0.08 ppm in the medium at the end of culture.
(9) The method according to any one of (6) to (8), wherein the copper ions in the medium at the end of culture are present at no more than 0.1 ppm.
(10) The method according to any one of (1) to (9), wherein the organism-derived culture medium additive is an animal- or plant-derived culture medium additive.
(11) The method according to any one of (1) to (9), wherein the organism-derived culture medium additive is a fish-derived culture medium additive.
(12) The method according to any one of (1) to (9), wherein the organism-derived culture medium additive is a fish meat hydrolyzate.
(13) The method according to any one of (1) to (12), wherein the organism-derived culture medium additive to be added to the culture medium has been preliminarily measured for the copper content.
(14) The method according to any one of (1) to (13), wherein the cell is an animal cell.
(15) The method according to (14), wherein the cell is a mammalian cell.
(16) The method according to (15), wherein the mammalian cell is a CHO cell.
(17) The method according to any one of (1) to (16), wherein the cell has been transfected with a gene coding for a desired protein.
(18) The method according to (17), wherein the desired protein is an antibody.
(19) The method according to (18), wherein the antibody is tocilizumab.
(20) A method of cell culture using an initial medium wherein an organism-derived culture medium additive with a measured copper content has been added to the initial medium.
(21) The method according to (20), wherein the method of culture is batch culture, fed-batch culture, continuous culture, batch culture, or semi-batch culture.
(22) The method according to (20), wherein the method of culture is fed-batch culture.
(23) A method of cell culture comprising the steps of:
 (1) preliminarily measuring the copper content in an organism-derived culture medium additive to be added to a medium; and
 (2) selecting the measured additive with a copper content of no more than 1 ppm and adding the same to an initial medium.
(24) A method of fed-batch cell culture comprising the steps of:
 (1) preliminarily measuring the copper content in an organism-derived culture medium additive to be added to a medium;
 (2) selecting the measured additive with a copper content of no more than 1 ppm and adding the same to a seed medium or an initial medium; and
 (3) selecting from the measured additives the one with a copper content of no more than 3 ppm and adding the same to a fed-batch medium.
(25) A process for producing a protein using the method of culture according to any one of (1) to (24).
(26) A process for producing a pharmaceutical composition containing a desired protein, comprising the steps of:
 (1) producing the desired protein by the production process according to (25); and
 (2) producing the pharmaceutical composition by mixing the desired protein produced in step 1) with a carrier and an additive that are pharmaceutically acceptable and formulating the same.
(27) A method of suppressing the generation of C-terminal amidated species in a desired protein by using the culture method according to any one of (1) to (24).
(28) The method according to (27), wherein the desired protein is an antibody.

Advantageous Effects of Invention

According to the present invention, organism-derived culture medium additives to be added to a seed culture medium, an initial medium or a fed-batch medium for use in fed-batch culture are preliminarily measured for their copper content, depending on which each additive is added to an appropriate medium, whereby variations in the amount of C-terminal amidated species in the produced protein can be controlled.

DESCRIPTION OF EMBODIMENTS

On the following pages, embodiments of carrying out the present invention are described in detail.

The present invention relates to a culture method characterized in that an organism-derived culture medium additive with a measured copper content is added to a medium for cell culture, as well as a process for protein production that uses such culture method to produce a protein by a cell.

Methods of cell culture are generally classified into batch culture, continuous culture, and fed-batch culture.

In batch culture, a small amount of seed culture broth is added to a medium and cells are proliferated without replenishing the medium with a fresh one or discharging the culture broth.

In continuous culture, a medium is continuously added and discharged during culture. Perfusion culture is also included in the continuous culture.

Fed-batch culture is a hybrid of batch culture and continuous culture and also called semi-batch culture; as in continuous culture, a medium is continuously or consecutively added during culture, but no continuous discharge of the culture broth is performed. The medium to be added in fed-batch culture (hereinafter referred to as "fed-batch medium") does not need to be identical to the medium already used in culture (hereinafter referred to as "initial medium"), and a dissimilar medium may be added or only a specified ingredient may be added.

In the present invention, any of batch culture, continuous culture and fed-batch culture may be employed, with fed-batch culture being preferred.

According to the usual procedure for producing a desired protein by cell culture, a seed medium containing cells is added in a specified amount to an initial medium and the cells are cultured. Further, in order to increase the production of the desired protein, a fed-batch medium is added during culture.

The seed medium refers to a medium in which cells that produce a desired protein (i.e., a working cell bank) are expansively cultured until the necessary cell count is obtained to transfer into a medium (initial medium) for eventual production of the desired protein. The initial medium generally refers to a medium in which the cells are cultured to produce the desired protein and which is used in the first stage of culturing the cells. The fed-batch medium generally refers to a medium that is added to the medium in which initial culture is being conducted. The fed-batch medium may be added in two or more divided portions. Alternatively, it may be added continuously or intermittently.

In the present invention, cells are subcultured in the seed medium and, thereafter, a specified amount of the cell-containing seed medium is added to the initial medium, in which the cells are cultured to produce the desired protein. Optionally, the fed-batch medium may be added one or more times to the medium in which culture is being conducted. Here, at least one of the seed medium, the initial medium and the fed-batch medium has an organism-derived culture medium additive added thereto, and it is preferred that the organism-derived culture medium additive has been added to all the media.

In one embodiment of the present invention, the organism-derived culture medium additive is added to all of the seed medium, the initial medium and the fed-batch medium. In another embodiment of the present invention, the organism-derived culture medium additive may be added to only the initial medium. In still another embodiment of the present invention, culture medium additives derived from different biological species may be added to the seed medium and the initial medium.

To give an exemplary culture method, cell culture is started in the initial medium and further the fed-batch medium is added at least once to the medium in which cell culture is being conducted, wherein an organism-derived culture medium additive with a measured copper content is added to at least one of the initial medium and the fed-batch medium.

Another exemplary culture method that can be adopted is characterized in that cell culture is started in a medium to which an organism-derived culture medium additive with a measured copper content has been added and further an organism-derived culture medium additive with a measured copper content is added at least once to the medium in which cell culture is being conducted. This culture method is one embodiment of fed-batch culture (involving the addition of only a specified ingredient).

While the ratio between the amount of the seed medium to be added to the initial medium and the amount of the initial medium is not particularly limited, the volume ratio of the seed medium, relative to the volume of the initial medium which is taken as unity, generally ranges from 0.1 to 1, preferably from 0.2 to 0.6, and more preferably from 0.3 to 0.5. The ratio between the amount of the initial medium and that of the fed-batch medium (i.e., the total amount of the fed-batch medium to be added to the initial medium in one performance of culture) is not particularly limited, either, but the volume ratio of the fed-batch medium, relative to the volume of the initial medium which is taken as unity, generally ranges from 0.01 to 10, preferably from 0.1 to 1, and more preferably from 0.2 to 0.3. The fed-batch medium may be added continuously or consecutively. When the fed-batch medium is added consecutively, the number of additions is not particularly limited and the fed-batch medium may be added either once or added in two or more divided portions.

The present invention is notably characterized in that the organism-derived culture medium additive to be added to the seed medium, the initial medium and/or the fed-batch medium has been preliminarily measured for its copper content. The respective organism-derived culture medium additives to be added to the seed medium, the initial medium and the fed-batch medium may come from the same production lot or different production lots. If desired, organism-derived culture medium additives from different production lots may be used in admixture. Since the copper content in the organism-derived culture medium additive is measured before preparing the medium, the way in which the respective lots of organism-derived culture medium additives to be added to media are used in the seed culture medium, the initial medium, the fed-batch medium, or use in admixture) can be determined in accordance with the measured copper content prior to media preparation.

Hereinafter, the respective organism-derived culture medium additives to be added to the seed medium, the initial medium and the fed-batch medium are sometimes referred to as the organism-derived culture medium additive for the seed medium, the organism-derived culture medium additive for the initial medium, and the organism-derived culture medium additive for the fed-batch medium.

The present inventors investigated how the copper contents in the respective organism-derived culture medium additives to be added to the seed medium, the initial medium and the fed-batch medium are related to the amount of C-terminal amidated species in the produced proteins. As it turned out, the copper contents in the organism-derived culture medium additives exerted greater effects on the amount of C-terminal amidated species in the produced proteins when they were added to the initial medium than when they were added to the seed medium and fed-batch medium. Hence, in order to control the variations in the amount of C-terminal amidated species in the proteins to be produced, it is desirable that the copper content of the organism-derived culture medium additive for the initial medium should vary by smaller degrees than the copper content of the organism-derived culture medium additive for the seed medium or fed-batch medium. It is also desirable that the copper content in the organism-derived culture medium additive for the initial medium is not higher than a specified concentration.

An exemplary embodiment of the present invention is a process for producing a protein by culture using either one of the seed medium, the initial medium and the fed-batch medium or two or more of these media, wherein any one of the seed medium, the initial medium and the fed-batch medium has added thereto an organism-derived culture medium additive with a measured copper content which is not higher than about 3 ppm. A preferred embodiment of the present invention is a process for producing a protein by culture using either one of the seed medium, the initial medium and the fed-batch medium or two or more of these media, wherein at least the initial medium has added thereto an organism-derived culture medium additive with a measured copper content which is not higher than 1 ppm, preferably not higher than 0.8 ppm, and more preferably not higher than 0.7 ppm.

In short, it is desirable that the copper content of the organism-derived culture medium additive for the initial medium is not higher than 1 ppm, preferably not higher than 0.8 ppm, and more preferably not higher than 0.7 ppm.

It is also desirable that the copper content of the organism-derived culture medium additive for the seed medium is not higher than 1 ppm, preferably not higher than 0.8 ppm, and more preferably not higher than 0.7 ppm.

As for the organism-derived culture medium additive for the fed-batch medium, its copper content is desirably not higher than 3 ppm.

To measure the copper content, any methods that are already known to skilled artisans may be employed. For example, measurement can be performed by emission spectro-photometric analysis using high-frequency inductively coupled plasma as a light source.

In the method of the present invention, it is desirable that the variations in the copper contents of medium ingredients other than the organism-derived culture medium additives to be added are smaller than the variations in the copper contents of the organism-derived culture medium additives to be added. Alternatively, it is desirable that the medium ingredients other than the organism-derived culture medium additives to be added have smaller copper contents than the organism-derived culture medium additives to be added.

When culture medium additives derived from two or more organisms are to be added, the culture medium additive(s) derived from the organism(s) already known to have low copper content(s) can be used without taking the trouble of measuring copper content.

According to the present invention, at least one organism-derived culture medium additive to be added to a medium is measured for its copper content and this makes it possible to control the amount of the C-terminal amidated species in the proteins to be produced.

Still another exemplary embodiment of the present invention is a culture method in which cell culture is started in the initial medium and further the fed-batch medium is added at least once to the medium in which cell culture is being conducted, wherein organism-derived culture medium additives with measured copper contents have been added to the initial medium and the fed-batch medium, respectively, so that the amount of copper ions in a medium at the start of cell culture or at the end of culture is adjusted to be not higher than a specified concentration. For example, at the start of cell culture, the initial medium preferably has a copper content of not greater than 0.02 ppm, more preferably not higher than 0.015 ppm; at the end of culture, the medium preferably contains not higher than 0.1 ppm of copper ions; the amount of copper ions derived from the fed-batch medium is preferably not higher than 0.08 ppm.

The organism-derived culture medium additives to be used in the present invention may be exemplified by culture medium additives derived from many animals and plants, as well as microorganisms including yeasts; specific examples include culture medium additives derived from mammals such as cattle, pig and sheep, culture medium additives derived from fishes such as bonito, sardine and cod, culture medium additives derived from plants such as wheat, soybean and rice, and culture medium additives derived from microorganisms such as yeast; preferred are additives derived from fishes or plants, and particularly preferred are additives derived from bonito, wheat, soybean, and yeast.

In a preferred embodiment, animal or plant derived enzymatic decomposition products may be used as the organism-derived culture medium additives in the present invention. The enzymatic decomposition products can be obtained by a process comprising enzymatically hydrolyzing the animal or plant tissue as the starting material and purifying the resulting decomposition product by centrifugation, filtration with a filter and the like. The common form of use is a spray-dried powder. For example, as for an enzymatic decomposition product in which fish is used as a starting material; the decomposition product may be produced by the process described in Japanese Patent No. 3822137 titled "Additives for Animal Cell Culture Media and Processes for Producing Proteins Using the Same."

The animal or plant derived enzymatic decomposition products that can be used in the present invention are specifically exemplified by those derived from mammals such as cattle, pig and sheep, those derived from fishes such as bonito, sardine and cod, and those derived from plants such as wheat, soybean and rice; preferred are those derived from fishes or plants, and particularly preferred are those derived from bonito, wheat, rice, and soybean.

Further, as is apparent from the Examples given later, the fish derived hydrolyzate to be used in the present invention has great variations in the content of copper ions among production lots, so the culture method of the present invention proves to be effective.

In the present invention, commercial organism-derived culture medium additives that are suitable for each protein production process or cell culture method may also be employed appropriately. Exemplary commercial organism-derived culture medium additives include those which are derived from bonito (e.g. Hy-Fish (FL) manufactured by Maruhachi Muramatsu, Inc.), wheat, soybean, yeasts, mammals (cattle, pig, sheep, etc.)

Suitable concentrations at which the organism-derived culture medium additives are added to the seed medium generally range from 0.5 to 30 g/L, preferably from 1 to 20 g/L, and more preferably from 2 to 10 g/L. Suitable concentrations at which the organism-derived culture medium additives are added to the initial medium generally range from 1 to 30 g/L, preferably from 3 to 20 g/L, and more preferably from 5 to 15 g/L. Suitable concentrations at which the organism-derived culture medium additives are added to the fed-batch medium generally range from 5 to 150 g/L, preferably from 10 to 120 g/L, and more preferably from 20 to 90 g/L.

In particular, when fish-derived culture medium additives are used, they are preferably added to the seed medium at concentrations of 2 to 5 g/L, preferably added to the initial medium at concentrations of 5 to 15 g/L, and preferably added to the fed-batch medium at concentrations of 30 to 75 g/L.

As for other ingredients in the media to be used in the present invention, those commonly used in cell (preferably animal cell) media may be employed appropriately. Examples include amino acids, vitamins, lipid factors, energy sources, osmotic pressure regulators, iron sources, and pH buffers. In addition to the ingredients listed above, for example, trace metal elements, surfactants, growth cofactors, and nucleosides may be added.

Specifically, the media to be used in the present invention may contain the following ingredients: amino acids such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, with L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, and L-valine being preferred: vitamins such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin B12, and ascorbic acid, with biotin, folic acid, lipoic acid, nicotinic acid amide, calcium pantothenate, pyridoxal hydrochloride, riboflavin, thiamine hydrochloride, vitamin B12, and ascorbic acid being preferred; lipid factors such as choline chloride, choline tartrate, linoleic acid, oleic acid, and cholesterol, with choline chloride being preferred; energy sources such as glucose, galactose, mannose, and fructose, with glucose being preferred; osmotic pressure regulators such as sodium chloride, potassium chloride, and potassium nitrate, with sodium chloride being preferred; iron sources such as iron EDTA, iron citrate, ferrous chloride, ferric chloride, ferrous sulfate, ferric sulfate, and ferric nitrate, with ferric chloride, iron EDTA, and iron citrate being preferred; and pH buffers such as sodium hydrogencarbonate, calcium chloride, sodium dihydrogenphosphate, HEPES and MOPS, with sodium hydrogencarbonate being preferred.

In addition to the ingredients listed above, for example, trace metal elements such as copper sulfate, manganese sulfate, zinc sulfate, magnesium sulfate, nickel chloride, tin chloride, magnesium chloride, and sodium silicate, with copper sulfate, zinc sulfate and magnesium sulfate being preferred; surfactants such as Tween 80 and Pluronic F68; growth cofactors such as recombinant insulin, recombinant IGF, recombinant EGF, recombinant FGF, recombinant PDGF, recombinant TGF-α, ethanolamine hydrochloride, sodium selenite, retinoic acid, and putrescine hydrochloride, with sodium selenite, ethanolamine hydrochloride, recombinant IGF, and putrescine hydrochloride being preferred; and nucleosides such as deoxyadenosine, deoxycitidine, deoxyguanosine, adenosine, citidine, guanosine, and uridine may be added. In the preferred examples of the present invention mentioned above, antibiotics such as streptomycin, penicillin G potassium and gentamicin, as well as pH indicators such as Phenol Red may also be contained.

In the present invention, the media to which the organism-derived culture medium additives are to be added are not particularly limited and any media may be employed. Common basal media contain copper in amounts approximately ranging from $\frac{1}{100}$ to $\frac{1}{10}$ of the copper content in additives for the media and such amounts alone are insufficient to affect the homogeneity of the antibody. For example, the copper content in basal media free of organism-derived ingredients and used in the Examples to be described later ranges from about 0.001 to about 0.01 ppm.

The media to be used in the present invention can be prepared from commercial animal cell culture media, such as D-MEM (Dulbecco's Modified Eagle Medium), D-MEM/F-12 1:1 Mixture (Dulbecco's Modified Eagle Medium: Nutrient Mixture F-12), RPMI 1640. CHO-S-SFM II (Invitrogen), CHO-SF (Sigma-Aldrich), EX-CELL 301 (TRH biosciences), CD-CHO (Invitrogen), IS CHO-V (Irvine Scientific), and PF-ACF-CHO (Sigma-Aldrich), with the organism-derived culture medium additives added thereto.

Other ingredients in media are suitably contained in the following amounts: 0.05-1500 mg/mL, for amino acids; 0.001-10 mg/mL for vitamins; 0-200 mg/mL for lipid factors; 1-20 g/mL for energy sources; 0.1-10000 mg/mL for osmotic pressure regulators; 0.1-500 mg/mL for iron sources; 1-10000 mg/mL for pH buffers; 0.00001-200 mg/mL for trace metal elements; 0-5000 mg/mL, for surfactants; 0.05-10000 μg/mL for growth cofactors; and 0.001-50 mg/mL for nucleosides. These amounts can be determined as appropriate for various factors including the type of the cell to be cultured and the type of the desired protein.

The pH of media varies with the cell to be cultured and suitable values are generally between 6.8 to 7.6, in most cases between 7.0 to 7.4.

The culture method of the present invention is not particularly limited and can be used to culture a variety of cells (e.g. bacterial, fungal, insect, plant, animal cells and the like). For example, COS or CHO cells into which genes coding for desired proteins have been incorporated by genetic engineering procedures or fusion cells typified by antibody-producing hybridomas of mouse-human, mouse-mouse, mouse-rat and the like can be cultured. The method of the present invention can also be used in culturing animal cells with a view to obtaining native proteins they produce, and it can even be applied to culture cells such as BHK and HeLa cells other than those mentioned above.

Animal cells that are particularly preferred in the present invention are CHO cells transfected with genes coding for desired proteins. The desired proteins are not particularly limited and may be of any types including antibodies (e.g. native, low-molecular weight, chimeric, and human antibodies), as well as physiologically active proteins (e.g. granulocyte colony stimulating factor (G-CSF), granulocyte macrophage colony stimulating factor (GM-SCF), erythropoietin, interferons, interleukins such as IL-1 and IL-6, t-PA, urokionase, senim albumin, blood coagulation factors and the like); antibodies are particularly preferred.

Antibodies that can be produced by the production process of the present invention include not only monoclonal antibodies derived from animals such as human, mouse, rat, hamster, rabbit and monkey, but also artificially modified gene recombinant antibodies such as chimeric, humanized and bispecific antibodies. The immunoglobulins of antibodies are not particularly limited and may be of any classes such as IgG (e.g. IgG1, IgG2, IgG3, IgG4 and the like), IgA, IgD, IgE, and IgM, with IgG and IgM being preferred when the antibodies are to be used as pharmaceuticals. In the present invention, the antibodies does not need to be whole antibodies and may include antibody fragments such as Fv, Fab and $F(ab)_2$ as well as low-molecular weight antibodies such as mono-, di- or higher-valent single-chain Fv (e.g. scFv or $sc(Fv)_2$) which have antibody's variable regions connected together by peptide- or other linkers.

Some animal cells simply need to be cultured to produce proteins while others require special culture procedures for protein production; in the latter case, the specific procedures or conditions may be determined as appropriate for the animal cell that is to be cultured. For example, given CHO cells transformed by genetic engineering procedures with a vector including a gene coding for a mouse-human chimeric antibody, the antibodies can be obtained in the medium under the conditions described later. The resulting product by the culture is then isolated and purified in the usual manner (see, for example, KOUTAI KOGAKU NYUMON (Introduction to Antibody Engineering), published by Chijin Shokan, p. 102-104; Affinity Chromatography Principles & Methods, Amersham Pharmacia Biotech Inc., p. 56-60) to obtain the desired protein.

Since the culture conditions vary with the type of the cell to be used, suitable conditions may be determined in an appropriate manner, CHO cells, for example, may usually be cultured in a gas-phase atmosphere at a $CO_2$ concentration of 0-40%, preferably 2-10%, at 30-39° C., preferably at about 37° C., for 1-14 days.

Various types of culture devices can be used to culture animal cells and they include, for example, fermenter-type, air lift-type, culture flask-type, spinner flask-type, microcarrier-type, fluidized bed-type, hollow fiber-type, roller bottle-type, and packed bed-type culture devices.

By culturing cells (preferably animal cells) in accordance with the method of the present invention, the amount of the C-terminal amidated species in the produced protein can be predicted. Hence, proteins that have a possibility of generating C-terminal amidated species can be controlled in terms of the amount of the C-terminal amidated species to be generated.

For example, by culturing CHO cells by the cell culture method of the present invention to produce antibodies, humanized antibody drugs (IgG1, IgG2, IgG3, and IgG4) can be controlled in the amount of the C-terminal amidated species.

To give a more specific example, the cell culture method of the present invention may be applied to the production of a humanized anti-IL-6 receptor antibody from cultured CHO cells, whereupon the humanized anti-IL-6 receptor antibody can be produced with a controlled amount of C-terminal prolinamide species. An even more specific example is to perform fed-batch culture with a fish meat derived culture medium additive (such as a bonito hydrolyzate) being added in specified amounts to the respective media of interest (seed, initial and fed-batch media). Here, production lots of the fish meat derived culture medium additive to be added to the initial medium are desirably selected so that its copper content will not exceed 1 ppm. While the fish meat derived culture medium additive with copper contents between zero to about 1.0 ppm can be used in any of the seed, initial and fed-batch media, those with copper contents between a concentration higher than 1 ppm (ca. 1.1 ppm) to 3.0 ppm can only be used in the fed-batch medium. The fish meat derived culture medium additive with copper contents higher than 3.0 ppm are desirably not used in the production of antibodies.

If the proteins produced by the method of the present invention have biological activities that warrant their use as pharmaceuticals, they may be formulated by being mixed with pharmaceutically acceptable carriers or additives to produce pharmaceutical compositions.

Examples of the pharmaceutically acceptable carriers and additives include: water; buffers; surfactants acceptable as pharmaceutical additives; pharmaceutically acceptable organic solvents; and others such as collagen, polyvinyl alcohol, polyvinylpyrrolidone, carboxyvinyl polymer, carboxymethyl cellulose sodium, poly(sodium acrylate), sodium alginate, water-soluble dextran, carboxymethyl starch sodium, pectin, methylcellulose, ethylcellullose, xanthan gum, gum Arabic, casein, agar, polyethylene glycol, diglyerin, glycerin, propylene glycol, petrolatum, paraffin, stearyl alcohol, stearic acid, human serum albumin (HSA), mannitol, sorbitol, and lactose.

From the above list, actual additives may be selected either alone or in appropriate combinations depending on the dosage form of a specific pharmaceutical composition but of course are not limited to the list. For example, when the pharmaceutical composition is to be used as an injectable preparation, the purified protein may be dissolved in a solvent such as physiological saline, a buffer solution or a glucose solution and to the solution, and there may be added an anti-adsorbent such as Tween 80, Tween 20, gelatin, or human serum albumin. Alternatively, the purified protein may be freeze-dried to prepare a formulation that is dissolved for reconstitution prior to use, and exemplary excipients for freeze-drying include sugar alcohols such as mannitol, and sugars such as glucose.

EXAMPLES

On the following pages, the present invention is described specifically by means of Examples and Referential Examples, which are given for illustrative purposes only and are by no means intended to limit the scope of the present invention.

Example 1

Correlation between Copper Content in Bonito Hydrolyzate and the Amounts of Inhomogeneous Components in the Antibodies Produced by Batch Culture Using the Bonito Hydrolyzate The following describes composition of the media and preparation procedures thereof.
Seed medium: To a medium free of animal- or plant-derived ingredients (12.3 g/L charged in powder form), a soybean hydrolyzate (3 g/L) and a wheat hydrolyzate (1 g/L) were added and dissolved to form a solution which was sterilized by filtration.
Initial medium: To a medium free of animal- or plant-derived ingredients (15.6 g/L charged in powder form), a bonito hydrolyzate (15 g/L) was added and dissolved to form a solution which was sterilized by filtration. In addition, the copper content of the bonito hydrolyzate was measured.

Cells: CHO cells capable of producing humanized PM-1 antibody (generic name: tocilizumab) that is a humanized anti-IL-6 receptor antibody prepared by a modification of the method described in Referential Example 2 of JP H8-99902 A using the human elongation factor Iα promoter described in Example of WO 92/19759 A; this antibody is in the class of IgG1.

The initial medium was charged into a flask-type cell culture device; to the initial medium, the above-described CHO cell line cultured in the seed medium was added at varying concentrations between 3.5 to 4.5×10⁵ cells/mL and culture was started under conditions of 37° C. and 5% $CO_2$. Of 50 mL of the culture broth, 10 mL was occupied by the seed medium and 40 mL by the initial medium. At day 7 of culture, the culture supernatant was subjected to affinity chromatography on a protein A column to purify the product antibody protein, which was then analyzed by cation chromatography to measure the content (%) of peaks for inhomogeneous components (Sub-1 peaks) that contained C-terminal prolinamide species as peak area ratios on the chromatograms. Cation chromatography was performed by using a column with cation-exchange resin, where peaks were separated and eluted in a buffer with a concentration gradient of salt. An ultraviolet and visible spectrophotometer was used to detect the peaks.

The copper content of the bonito hydrolyzate was measured by emission spectro-photometric analysis using high-frequency inductively coupled plasma as a light source.

Figure 1:
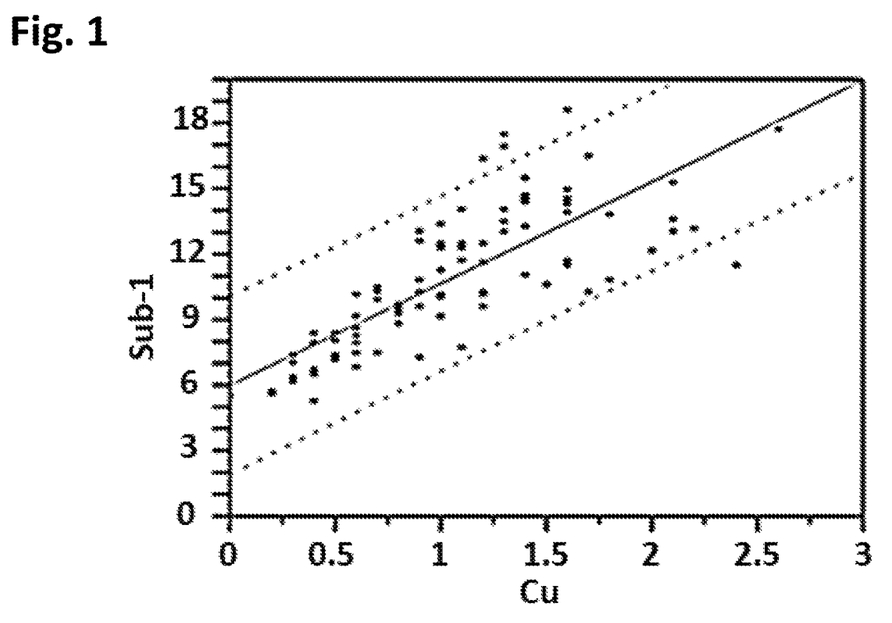
FIG. 1 shows the correlation between the content (%) of inhomogeneous components' peaks (Sub-1 peaks) containing C-terminal prolinamide species found by ion-exchange chromatography of an antibody protein produced from CHO cells as cultured in a medium, to which 15 g/L of a commercial bonito hydrolyzate of plural lots had been added, and the copper content (ppm) of each hydrolyzate lot.

The content (%) of Sub-1 peaks was plotted against the copper content (ppm) of the animal or plant derived hydrolyzate (bonito hydrolyzate) used in the culture and the constructed graph is shown in FIG. 1.

A positive correlation ($R^2$ adjusted for the degrees of freedom=0.58) was observed between the copper content and the peaks for inhomogeneous components.

Example 2

Correlation between the Amount of Copper Addition and the Amounts of Inhomogeneous Components in the Antibodies Produced by Batch Culture Using Bonito Hydrolyzate The following describes composition of the media and preparation procedures thereof.

Seed medium: Same as in Example 1.

Initial media: Same as in Example 1, except for the following: A bonito hydrolyzate containing 0.5 ppm Cu (Lot A) was used either alone or in admixture with copper sulfate that was added in such amounts that the calculated copper content of the bonito hydrolyzate would be equivalent to 3.5, 7 and 10 ppm, and culture was performed as in Example 1; a bonito hydrolyzate containing 3.5 ppm Cu (Lot B) was used either alone or in admixture with copper sulfate that was added in such amounts that the calculated copper content of the bonito hydrolyzate would be equivalent to 7 and 10 ppm, and culture was performed as in Example 1. The final concentrations of copper in the initial media were calculated to have the following values: 0.0075 ppm Cu for the addition of the bonito hydrolyzate containing 0.5 ppm Cu; 0.0525 ppm Cu for the addition of the bonito hydrolyzate containing 3.5 ppm Cu; 0.105 ppm Cu for the addition of the bonito hydrolyzate containing 7 ppm Cu; and 0.15 ppm Cu for the addition of the bonito hydrolyzate containing 10 ppm Cu.

Cells: Same as in Example 1.

The experimental method was also the same as in Example 1.

Figure 2:
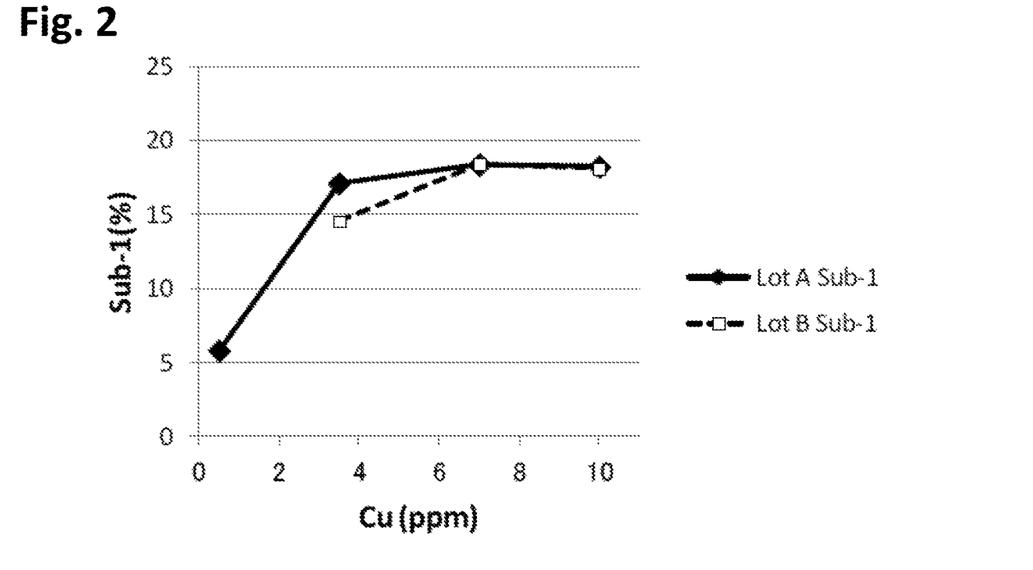
FIG. 2 shows the increase in the content (%) of Sub-1 peaks in the produced antibody protein upon addition of copper to a medium, with the values of Cu (ppm) on the horizontal axis representing the sum content of the copper added.

The results are shown in FIG. 2.

CHO cells were cultured in the medium to which 15 g/L of bonito hydrolyzate Lot A (Cu content=0.5 ppm) had been added and in the medium prepared by adding copper sulfate to Lot A in such amounts that its calculated copper content would be equivalent to 3.5, 7 and 10 ppm, as well as in the medium to which 15 g/L of bonito hydrolyzate Lot B (Cu content=3.5 ppm) had been added and in the medium prepared by adding copper sulfate to Lot B in such amounts that its calculated copper content would be equivalent to 7 and 10 ppm; the antibody proteins produced in those media by the cells were purified by ion exchange chromatography and the content (%) of peaks for inhomogeneous components containing C-terminal prolinamide species (Sub-1 peaks) was plotted against the Cu content derived from the bonito hydrolyzate as well as against the sum of this content and the added Cu content.

As FIG. 2 shows, the amount of the peaks for inhomogeneous components increased with increasing copper content. Thus, Example 2 also showed that the amount of inhomogeneous components in the antibody increased with the increasing copper content in the media to which the bonito hydrolyzate had been added.

Example 3

Effect of the Copper Content in Bonito Hydrolyzates Added to the Seed, Initial and Fed-Batch Media on the Amounts of Inhomogeneous Components in Antibodies Produced by Fed-Batch Culture Using the Bonito Hydrolyzates The following describes composition of the media and preparation procedures thereof.

Seed medium: To a medium free of animal- or plant-derived ingredients, a bonito hydrolyzate (3 g/L) was added and dissolved to form a solution which was sterilized by filtration.

Initial medium: To a medium free of animal- or plant-derived ingredients, a bonito hydrolyzate (15 g/L) was added and dissolved to form a solution which was sterilized by filtration.

Fed-batch medium: To a medium free of animal- or plant-derived ingredients, a bonito hydrolyzate (75 g/L) was added and dissolved to form a solution which was sterilized by filtration. In a separate step, the copper content of the bonito hydrolyzate was measured.

Cells: Same as in Example 1.

The seed medium was charged into a jar-type cell culture device; to the seed medium, the above-noted CHO cell line was added at the concentration of 3×10⁶ cells/mL and culture was started under conditions of 37° C. and 20% $CO_2$. At day 3 of culture, the seed culture broth was added to the initial medium that had been charged into a jar-type cell culture device, in such an amount that the volume ratio of the seed culture broth to the initial medium would be 1:2.2, and culture was continued under conditions of 37° C. and 10% $CO_2$. Starting at day 2 of culture, the fed-batch medium was added in a cell-density dependent manner. Out of 1 L of the final culture broth, 250 mL was occupied by the seed medium, 550 mL was occupied by the initial medium, and 200 mL was occupied by the fed-batch medium. At day 7 of culture, the culture supernatant was subjected to affinity chromatography on a protein A column and ion exchange chromatography to purify the produced antibody protein, which was then analyzed by cation chromatography to measure the content (%) of peaks for inhomogeneous components (Sub-1 peaks) that contained C-terminal prolinamide species.

The copper content of each bonito hydrolyzate was measured by emission spectro-photometric analysis using high-frequency inductively coupled plasma as a light source. The bonito hydrolyzate lot containing 1.3 ppm Cu was designated as a high-Cu content lot whereas the bonito hydrolyzate lot containing 0.6 ppm Cu was designated as a low-Cu content lot.

The high-Cu content lot (1.3 ppm Cu) or the low-Cu content lot (0.6 ppm Cu) was added to the seed medium, initial medium and fed-batch medium in amounts of 3 g/L, 15 g/L and 75 g/L, respectively, and the resulting 8 combinations were measured for the content (%) of Sub-1 peaks in the antibody proteins produced in the media by the fed-batch cultured CHO cells; the results are shown in the following table.

TABLE 1

| Seed culture medium | Initial medium | Fed-batch medium | Sub-1 (%) | Cu concentration (ppm) |
|---|---|---|---|---|
| Cu content high | Cu content high | Cu content high | 13.4 | 0.0312 |
| Cu content high | Cu content high | Cu content low | 9.8 | 0.0207 |
| Cu content high | Cu content low | Cu content high | 7.7 | 0.0254 |
| Cu content high | Cu content low | Cu content low | 6.4 | 0.0149 |
| Cu content low | Cu content high | Cu content high | 11.9 | 0.0307 |
| Cu content low | Cu content high | Cu content low | 10.6 | 0.0202 |
| Cu content low | Cu content low | Cu content high | 6.9 | 0.0249 |
| Cu content low | Cu content low | Cu content low | 5.8 | 0.0144 |

The "copper concentration" in the rightmost column of the table refers to the final Cu ion concentrations after the addition of the respective initial and fed-batch media.

Figure 3:
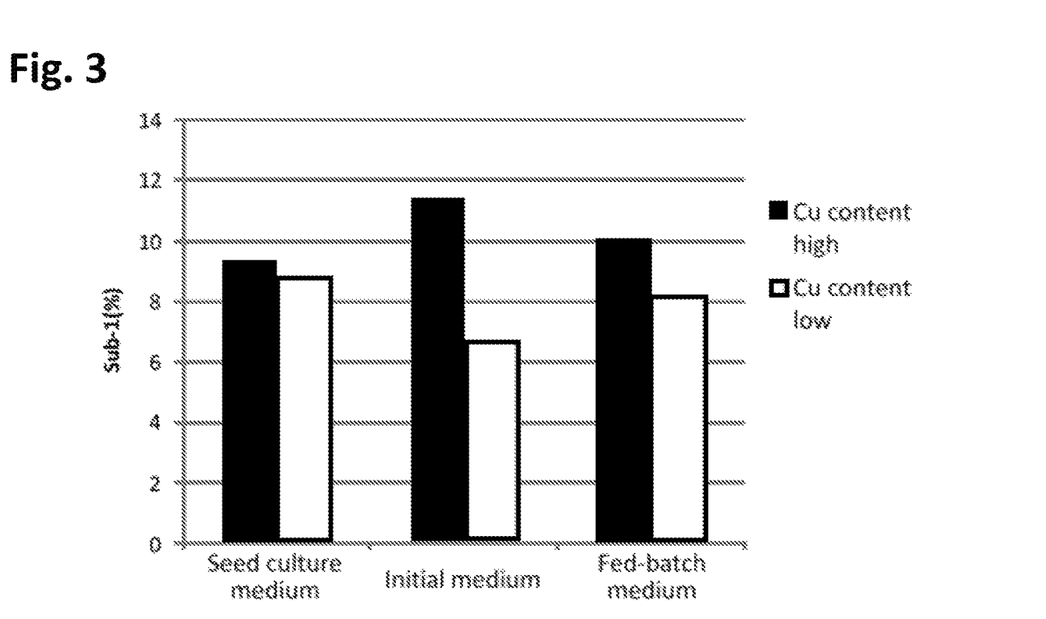
FIG. 3 shows the average values of the content (%) of Sub-1 peaks in the antibody proteins obtained by culture, using a bonito hydrolyzate of either high or low copper content for each of a seed culture medium, an initial medium, and a fed-batch medium.

FIG. 3 is a graph showing the average values of Sub-1 peak content (%) as obtained by culture, wherein seed culture medium, initial medium and fed-batch medium were added the bonito hydrolyzate of the high- or low-Cu content lot, respectively.

The Cu content in the bonito hydrolyzate exerted small effects on the Sub-1 peak content when it was added to the seed and fed-batch media whereas it exerted large effects when it was added to the initial medium.

From these results, it was shown that the copper contents in the seed, initial and fed-batch media caused varying effects on the content (%) of peaks for inhomogeneous components (Sub-1 peaks) that contained C-terminal prolinamide species in the produced antibody proteins.

Example 4

Correlation Between Copper Content in Bonito Hydrolyzates and the Amounts of Inhomogeneous Components in the Antibodies Produced by Fed-Batch Culture Using the Bonito Hydrolyzates The following describes composition of the media and preparation procedure thereof.

Seed medium: Same as in Example 3.
Initial medium: Same as in Example 3.
Fed-batch medium: Same as in Example 3. In a separate step, the copper content of the bonito hydrolyzate was measured.
Cells: Same as in Example 1.

The seed medium was charged into a jar-type cell culture device; to the seed medium, the above-noted CHO cell line was added at varying concentrations between 1.6 to $2.5 \times 10^5$ cells/mL and culture was started under conditions of 37° C. and pH 7.00-7.20. At day 3 of culture, the seed culture broth was added to the initial medium that had been charged into a jar-type cell culture device, in such an amount that the volume ratio of the seed culture broth to the initial medium would be 1:2.2, and culture was continued under conditions of 37° C. and pH 7.00-7.20. Starting at day 2 of culture, the fed-batch medium was added in a cell-density dependent manner. At day 7 of culture, the culture supernatant was subjected to affinity chromatography on a protein A column and ion exchange chromatography to purify the produced antibody protein, which was then analyzed by cation chromatography to measure the content (%) of peaks for inhomogeneous components (Sub-1 peaks) that contained C-terminal prolinamide species.

The copper content of each bonito hydrolyzate was measured by emission spectro-photometric analysis using high-frequency inductively coupled plasma as a light source.

Figure 4:
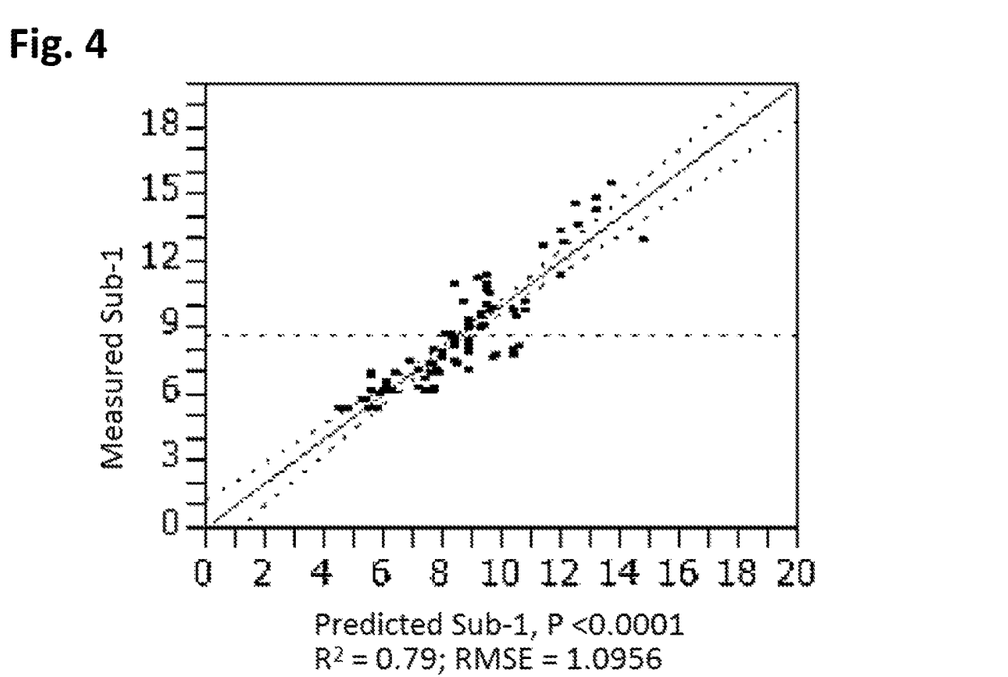
FIG. 4 shows a regression expression obtained by multiple regression analysis with the Sub-1 peak content (%) in the antibody proteins produced by CHO cells in the media being the objective variable and the copper contents in the bonito hydrolyzates added to the seed culture medium, the initial medium, and the fed-batch medium being the explanatory variables, wherein the CHO cells were cultured by the fed-batch culture using a seed culture medium to which a bonito hydrolyzate was added in 3 g/L, an initial medium to which a bonito hydrolyzate was added in 15 g/L, and a fed-batch medium to which a bonito hydrolyzate was added in 75 g/L. Since no statistically significant difference was observed between the copper content in the seed culture medium and the content of Sub-1 peaks in the analysis, the regression expression in FIG. 4 was calculated without using the copper content in the seed culture medium.

In FIG. 4, one dot represents one production run. In each production run, the respective media (seed medium, initial medium and fed-batch medium) used different bonito hydrolyzate lots, which were measured for their copper content before each medium was prepared.

A regression expression was obtained by multiple regression analysis, with the content (%) of peaks for inhomogeneous components (Sub-1 peaks) containing C-terminal prolinamide species being the objective variable and the copper contents in the animal- or plant-derived hydrolyzates (bonito hydrolyzates) added to the seed culture medium, initial medium and fed-batch medium being the explanatory variables.

Predicted Sub-1 (%)=2.13+3.83×[Cu content (ppm) in the bonito hydrolyzate added to the initial medium]+2.78×[Cu content (ppm) in the bonito hydrolyzate added to the fed-batch medium]

The present Example showed that the copper content in the seed culture medium exerted no effects on the objective variable.

As FIG. 4 shows, the copper contents in the bonito hydrolyzate added to the initial medium and fed-batch medium can be used for predicting the content (%) of peaks for inhomogeneous components (Sub-1 peaks) containing C-terminal prolinamide species.

It should be noted that all publications, patents and patent applications cited herein are incorporated herein by reference.

INDUSTRIAL APPLICABILITY

In accordance with the present invention, changes in the amounts of C-terminal amidated species of protein drugs due to variations in the content of copper in organism derived hydrolyzates used for production of the drugs can be controlled, enabling the supply of protein drugs of consistent quality.

The invention claimed is:
1. A method of cell culture comprising
   (1) determining the copper content of a meat hydrolysate of bonito, sardine or cod and selecting the meat hydrolysate having a copper content of no more than 1 ppm;
   (2) preparing an initial medium comprising the meat hydrolysate;
   (3) adding a seed culture comprising a CHO cell capable of producing tocilizumab to the initial medium to produce an initial culture; and
   (4) culturing the CHO cell in the initial culture, wherein the initial culture at the start of the culturing has a copper content no more than 0.02 ppm, wherein the method produces tocilizumab, and wherein C-terminal amidation of tocilizumab is reduced compared to culturing the CHO cell in an initial culture that has a copper content of more than 0.02 ppm at the start of the culturing.

2. The method according to claim 1, wherein the initial culture at the start of the culturing has a copper content no more than 0.015 ppm.

3. The method according to claim 1, wherein the seed culture comprises a seed medium comprising a meat hydrolysate of bonito, sardine or cod having a copper content of no more than 1 ppm.

4. The method according to claim 1, wherein the method of culture is batch culture, fed-batch culture, continuous culture, or semi-batch culture.

5. The method according to claim 1, wherein the method of culture is fed-batch culture.

6. The method according to claim 5, further comprising adding a feed medium to the initial culture to produce a fed culture, wherein the feed medium comprises a meat hydrolysate of bonito, sardine or cod having a copper content of no more than 3 ppm.

7. The method according to claim 6, wherein the fed culture at the end of the culturing has a copper content no more than 0.1 ppm.

8. A process for producing a pharmaceutical composition containing tocilizumab, comprising the steps of:

(1) producing the desired protein tocilizumab by the production process according to claim 1; and (2) producing the pharmaceutical composition by mixing tocilizumab produced in step (1) with a carrier and an additive that are pharmaceutically acceptable and formulating the same.

* * * * *